United States Patent [19]

Arlt et al.

[11] Patent Number: 5,068,300
[45] Date of Patent: Nov. 26, 1991

[54] BIFUNCTIONAL STILBENE COMPOUNDS CONTAINING AT LEAST ONE Z-CONFIGURATED STILBENE GROUP, PROCESS FOR THEIR PREPARATION AND THEIR USE FOR THE PREPARATION OF POLYMERS

[75] Inventors: Dieter Arlt, Cologne; Axel Bader, Bergisch Gladbach; Volker Eckhardt, Krefeld, all of Fed. Rep. of Germany

[73] Assignee: Bayer Aktiengesellschaft, Leverkusen, Fed. Rep. of Germany

[21] Appl. No.: 599,258

[22] Filed: Oct. 19, 1990

Related U.S. Application Data

[62] Division of Ser. No. 498,408, Mar. 26, 1990, abandoned.

[30] Foreign Application Priority Data

Apr. 7, 1989 [DE] Fed. Rep. of Germany ....... 3911221

[51] Int. Cl.$^5$ .............................................. C08F 22/02
[52] U.S. Cl. ............................ 526/318.2; 526/317.1;
526/318.1; 526/318.3; 528/298; 528/302;
528/303; 528/304; 528/305; 528/306; 562/480
[58] Field of Search ................. 526/318.1; 560/86, 76,
560/77; 528/176, 298

[56] References Cited

U.S. PATENT DOCUMENTS

| | | | |
|---|---|---|---|
| 3,860,584 | 1/1975 | Meyer | 548/219 |
| 3,935,195 | 1/1976 | Crounse | 546/115 |
| 3,954,705 | 5/1976 | Ashe | 525/207 |
| 4,179,578 | 12/1979 | Fleck | 560/76 |
| 4,414,382 | 11/1983 | Morris | 528/298 |
| 4,526,822 | 7/1985 | Morris | 428/35 |
| 4,654,412 | 3/1987 | Calundann | 528/176 |
| 4,666,627 | 5/1987 | Meyer | 252/301.22 |
| 4,713,472 | 12/1987 | Van Sickle | 560/53 |
| 4,785,128 | 11/1988 | Guglielmetti | 558/411 |
| 4,847,407 | 7/1989 | Morris | 560/86 |

OTHER PUBLICATIONS

A. Segnitz, Houben-Weyl, vol. 13/9b, p. 987 et seq.
V. Jäger, Houben-Weyl, vol. V/2a, pp. 405 and 649.
Cram, J. C. and Hammond, G. S., Organic Chemistry, McGraw-Hill, pp. 223–224.

*Primary Examiner*—Joseph L. Schofer
*Assistant Examiner*—Fred Zitomer
*Attorney, Agent, or Firm*—Connolly and Hutz

[57] ABSTRACT

New Z-stilbene compounds and a process for their preparation are disclosed wherein the compounds correspond to the following formulae:

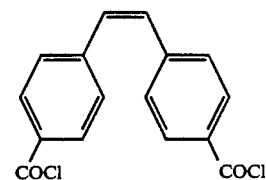

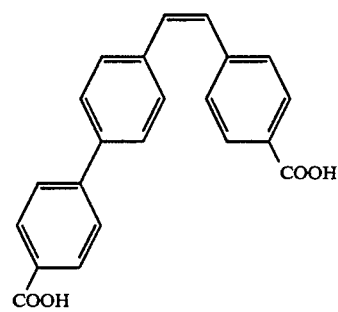

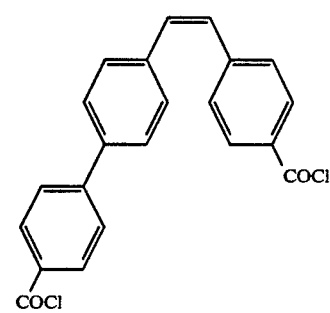

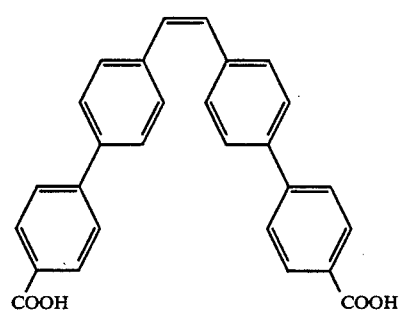

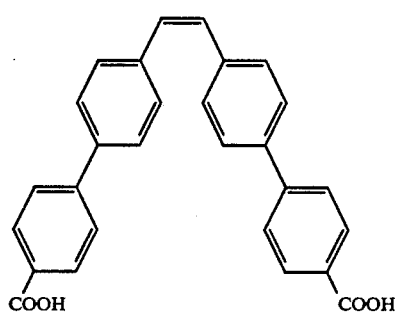

(Abstract continued on next page.)

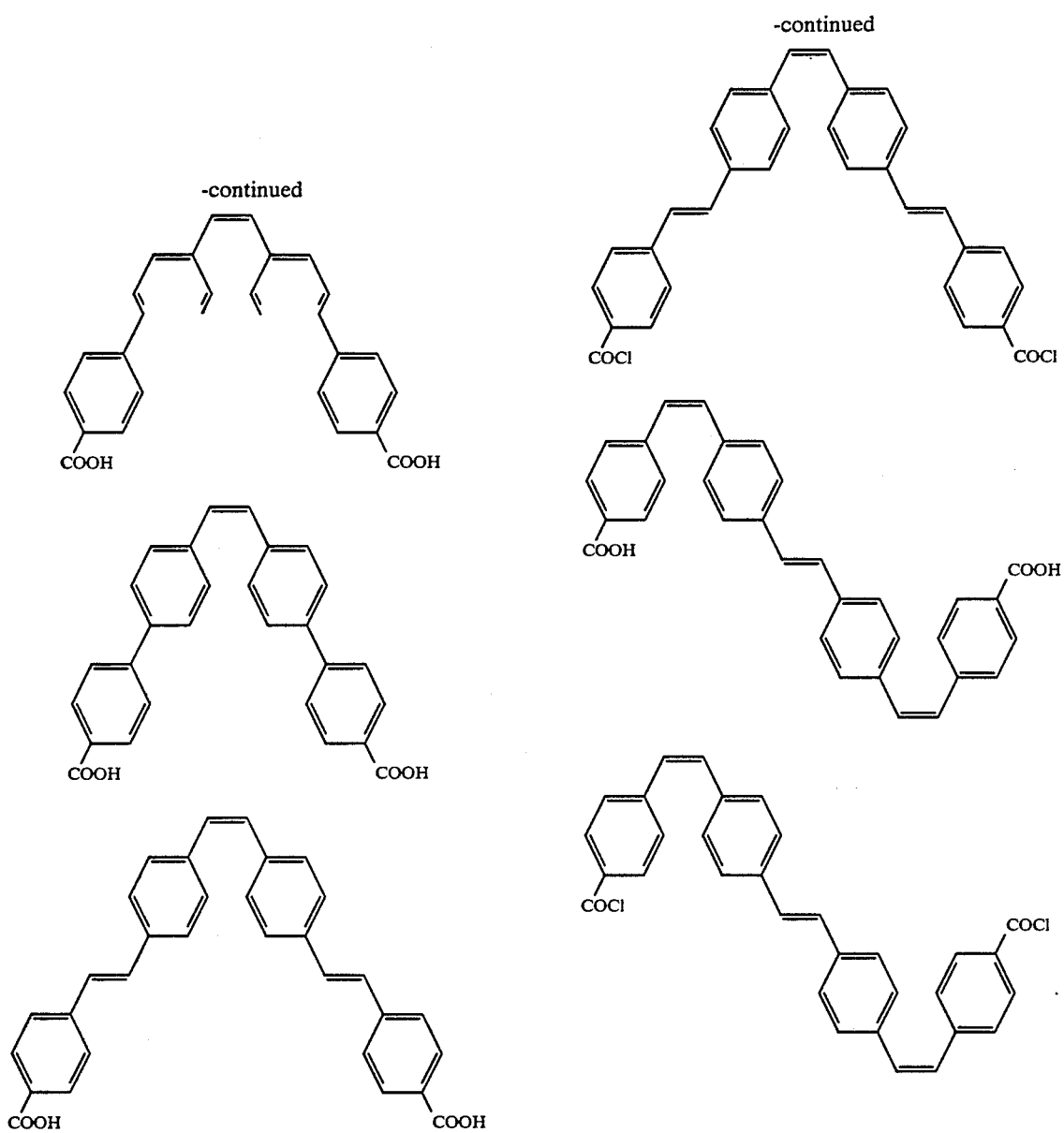
1 Claim, No Drawings

BIFUNCTIONAL STILBENE COMPOUNDS CONTAINING AT LEAST ONE Z-CONFIGURATED STILBENE GROUP, PROCESS FOR THEIR PREPARATION AND THEIR USE FOR THE PREPARATION OF POLYMERS

This application is a division of application Ser. No. 07/498,408 filed Mar. 26, 1990, now abandoned.

This invention relates to a process for the preparation of bifunctional Z-stilbene compounds, to new bifunctional Z-stilbene compounds and to the use of the Z-stilbene compounds for the preparation of polymers.

Z(cis)-stilbenes may be prepared by, for example, subjecting aryl aldehydes and aryl acetic acids to a Perkin condensation and decarboxylating the resulting cis-$\alpha,\beta$-diarylacrylic acids in quinoline in the presence of copper chromite at temperatures of about 200° C. (see F. Merger in Houben-Weyl, Vol. V/1b, page 308). This process does not always give rise to pure Z-stilbenes but to products containing a certain amount of the corresponding E(trans) stilbenes, the removal of which requires an elaborate procedure of chromatography or crystallisation and is not always complete. Another disadvantage of the process lies in the high temperatures (about 200° C.) required for decarboxylation, which may give rise to side reactions. The yields are only moderate and the range of variation of the reaction sequence is small due to the fact that some substituted aryl halides and aryl acetic acids are difficultly obtainable.

The synthesis of alkyl substituted Z-stilbenes is described by E. B. Merkushev and T. S. Skorokhodova in Zhurnal Organicheskoi Khimii, Vol. 18, No. 2, pages 355–359. The starting materials used for this synthesis are alkyl iodobenzenes which react with acetylene in the presence of Pd catalysts to yield di(alkylaryl)acetylenes which are subsequently stereo specifically hydrogenated to Z-stilbenes.

One disadvantage of this process is the use of the expensive and difficultly obtainable aryl iodides. The reaction has only been described for iodobenzene or alkyl substituted iodobenzenes and is on the whole suitable only for the preparation of the corresponding symmetric dialkyl substituted Z-stilbenes.

A process has now been found for the preparation of bifunctional stilbene compounds containing at least one Z-configurated stilbene group and corresponding to the following formula

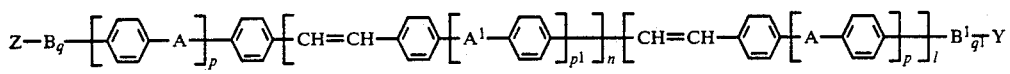

wherein
Z and Y may be identical or different and denote COOR, COR, COCl, OCOCl, NCO, NRCOCl, NHR, OR or Cl, where R=hydrogen or $C_1$-$C_8$-alkyl,
A and $A^1$ are identical or different and denote a chemical bond or CH=CH,
B denotes

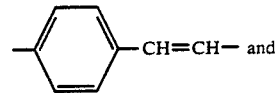

$B^1$ denotes

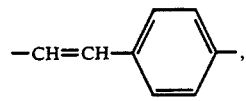

l stands for 0 or 1,
p and $p^1$ stand for 0 or 1,
q and $q^1$ stand for 0 or 1 and
n stands for 0, 1 or 2,
characterised in that compounds corresponding to the following formula

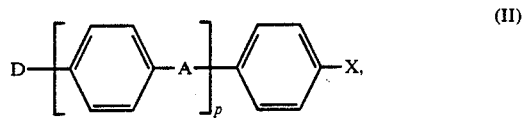

wherein
A and p have the meaning indicated above,
D denotes $COOR^1$, $COR^1$, $NHR^2$, $NO_2$, $OR^3$, Cl or Br, where $R^1$=hydrogen or branched or straight chained $C_1$-$C_8$-alkyl, $R^2$=OAc, $COOC_2H_5$ or another suitable protective group and $R^3$=OAc,

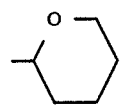

or another suitable protective group and
X stands for bromine or iodine are reacted with an acetylene corresponding to the following formula $$HC\equiv C\text{-}R^4 \qquad (III),$$

wherein $R^4$ stands for

or $Si(R^5)_3$, where $R^5$ and $R^6$=$C_1$-$C_4$-alkyl,
at temperatures from 30° to 160° C. in the presence of a palladium catalyst and a base, the resulting compounds are converted in the presence of a base into compounds corresponding to the following formula

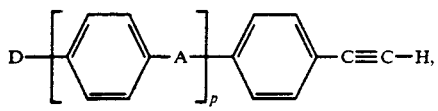

wherein D, A and p have the meanings indicated above, and the compounds of formula (IV) are then reacted with compounds corresponding to the following formula

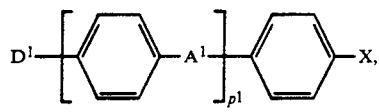

wherein
$D^1$, $A^1$ and $p^1$ have the meanings described for A, D and p and
X stands for bromine or iodine
at temperatures from 30° to 160° C. in the presence of a palladium catalyst and a base and the resulting acetylene compounds are reduced with hydrogen or another reducing agent in the presence of catalysts to form Z-stilbene compounds corresponding to the following formula

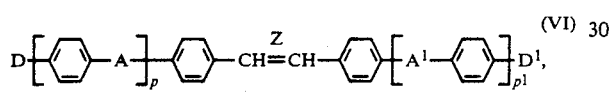

wherein D, $D^1$, A, $A^1$ and p and $p^1$ have the meanings indicated above, and the functional groups D and $D^1$ are converted into the above mentioned functional groups Z and Y of formula (I) in known manner or when D and $D^1$ stand for at least one bromine atom, the Z-stilbene compounds of formula (VI) are reacted with compounds corresponding to the following formula $$H_2C=CHR^7 \qquad (VII)$$

wherein
$R^7$ stands for hydrogen or

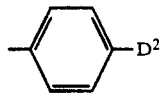

where $D^2$ has the meaning given above for $D^1$ at temperatures from 30° to 160° C. in the presence of a palladium catalyst and a base, and the functional groups D, $D^1$ and $D^2$ are converted into the functional groups Z and Y of formula (I) in the usual manner or the compounds of formula (IV) are reacted with compounds corresponding to the following formula

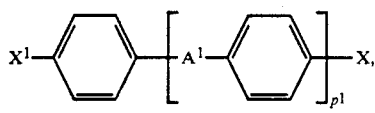

wherein
$A^1$ X and $p^1$ have the meanings indicated above and
$X^1$ stands for bromine or iodine at temperatures from 30° to 160° C. in the presence of a palladium catalyst and a base and the resulting acetylene compounds are then reduced to the corresponding Z-stilbene compounds with hydrogen or other reducing agents in the presence of catalysts and the functional groups D are then converted into functional groups Z and Y of formula (I) in known manner.

The reaction of the aromatic halides of the general formula II with acetylenes of formula (III) may be carried out by a method which is already known in principle (see e.g. A. Segnitz in Houben-Weyl Vol. 13/9b, pages 987 et seq). According to this method, the reaction is carried out in the presence of a palladium catalyst and the compound which is basic in reaction, optionally in the presence of a cocatalyst, a phosphane and a solvent and/or diluent at temperatures of about 30° to 160° C., preferably from 40° to 130° C.

This reaction gives rise to compounds corresponding to the following general formula (IX)

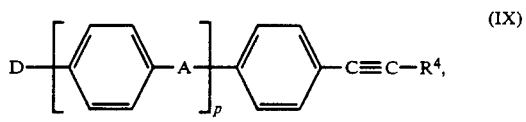

wherein D, A, p and $R^4$ have the meanings indicated above.

Examples of preferred aromatic halides of formula (II) include those in which A stands for a chemical bond or CH=CH, X stands for bromine or iodine, p stands for 0 or 1 and D stands for $COOR^1$, $COR^1$, $NHR^2$, $NO_2$, $OR^3$, Cl or Br, where $R^1$=hydrogen or branched or straight chained $C_1$-$C_8$-alkyl, $R^2$=OAc, $COOC_2H_5$ or another suitable protective group and $R^3$=OAc,

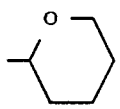

or another suitable protective group.

The following are given as examples of aromatic halides corresponding to formula (II): 4-Bromobenzoic acid, 4-bromobenzoic acid methyl ester 4-bromobenzoic acid ethyl ester, 4-bromobenzoic acid-n-propyl ester, 4-bromobenzoic acid-i-propyl ester, 4-bromobenzoic acid-n-butyl ester, 4-bromobenzoic acid-i-butyl ester 4-bromobenzoic acid tert.-butyl ester, 4-bromobenzoic acid-n-pentyl ester, 4-bromonitrobenzene, 4-bromobenzaldehyde, 4-acetoxybromobenzene, 4-acetoxy iodobenzene, 4-bromophenyl tetrahydropyranyl ether, 4-iodophenyl tetrahydropyranyl ether, 1,4-dibromobenzene, 1-bromo-4-iodobenzene, 4-bromoacetophenone, (4-bromophenyl)-ethyl) ketone, (4-bromophenyl)-n-propyl ketone, (4-bromophenyl)-i-propyl ketone, (4-bromophenyl)-n-butyl ketone, 4-bromoacetanilide, 4-iodoacetanilide, 4-bromophenyl carbamic acid ethyl ester, 1-bromo-4-chlorobenzene, 1-chloro-4-iodobenzene, 4-bromobiphenyl-4'-carboxylic acid methyl ester, 4-bromobiphenyl-4'-carboxylic acid ethyl ester, 4-bromobiphenyl-4'-carboxylic acid n-propyl ester, 4-bromobiphenyl-4'-carboxylic acid i-propyl ester, 4-bromobiphenyl-4'-carboxylic acid n-butyl ester, 4-bromobiphenyl-4'-carboxylic acid i-butyl ester, 4-bromobiphenyl-4'-carboxylic acid tert.-butyl ester, 4-bromobiphenyl-4'-carboxylic acid-n-pentyl ester, 4-bromo-4'-nitrobiphenyl, 4-acetoxy-4'-bromobiphenyl, 4-bromobiphenyl-4'-tetrahydropyranyl ether, 4-bromo-4'-iodobiphenyl, 4,4'-dibromobiphenyl, 4-bromo-4'-chlorobiphenyl, (4-bromobiphenyl-4'-yl)-methyl ketone, (4-bromobiphenyl-4'-yl)-ethyl ketone, (4-bromobiphenyl-4'-yl)-n-propyl ketone (4-bromobiphenyl-4'-yl)-i-propyl ketone, (4-bromobiphenyl-4'-yl)-n-butyl ketone, 4-acetamino-4'-bromobiphenyl, 4-bromobiphenyl-4'-carbamic acid ethyl ester, 4-bromostilbene-4'-carboxylic acid methyl ester, 4-bromostilbene-4'-carboxylic acid ethyl ester, 4-bromostilbene-4'-carboxylic acid n-propyl ester, 4-bromostilbene-4'-carboxylic acid n-butyl ester, 4-bromostilbene-4'-carboxylic acid i-propyl ester, 4-bromostilbene-4'-carboxylic acid i-butyl ester, 4-bromostilbene-4'-carboxylic acid tert.-butyl ester, 4-bromostilbene-4'-carboxylic acid n-pentyl ester, 4-bromo-4'-nitrostilbene, 4-acetoxy-4'-bromostilbene, 4-bromostilbene-4'-tetrahydropyranyl ether, 4-bromo-4'-iodostilbene, 4,4'-dibromostilbene, 4-bromo-4'-chlorostilbene, (4-bromostilbenyl-4')-methyl ketone, (4-bromostilbenyl-4')-ethyl ketone, (4-bromostilbenyl-4')-n-propyl ketone, (4-bromostilbenyl-4') i-propyl ketone, (4-bromostilbenyl-4')-n-butyl ketone, 4-acetamino-4'-bromostilbene and 4-bromostilbene-4'-carbamic acid ethyl ester, preferably 4-bromobenzoic acid, 4-bromobenzoic acid methyl ester, 4-bromobenzoic acid ethyl ester, 4-bromobenzoic acid n-propyl ester, 4-bromobenzoic acid i-propyl ester, 4-bromobenzoic acid n-butyl ester, 4-bromobenzoic acid i-butyl ester, 4-bromobenzoic acid tert.-butyl ester, 4-bromonitrobenzene, 4-bromobenzaldehyde, 4-acetoxybromobenzene, 4-acetoxyiodobenzene, 4-bromophenyl tetrahydropyranyl ether, 4-iodophenyl tetrahydropyranyl ether, 1,4-dibromobenzene, 1-bromo-4-iodobenzene, 4-bromoacetophenone, (4-bromophenyl)ethyl ketone, (4-bromophenyl)-n-propyl ketone, 4-bromoacetanilide, 4-iodoacetanilide, 4-bromophenyl carbamic acid ethyl ester, 1-bromo-4-chlorobenzene, 4-bromobiphenyl-4'-carboxylic acid methyl ester, 4-bromobiphenyl-4'-carboxylic acid ethyl ester, 4-bromobiphenyl-4'-carboxylic acid n-propyl ester, 4-bromobiphenyl-4'-carboxylic acid i-propyl ester, 4-bromobiphenyl-4'-carboxylic acid n-butyl ester, 4-bromobiphenyl-4'-carboxylic acid i-butyl ester, 4-bromobiphenyl-4'-carboxylic acid tert.-butyl ester, 4-bromo-4'-nitrobiphenyl, 4-acetoxy-4'-bromobiphenyl, 4-bromo-4'-iodobiphenyl, 4,4'-dibromobiphenyl, 4-bromo-4'-chlorobiphenyl, (4-bromobiphenyl-4'-yl)-methyl ketone, (4-bromophenyl-4'-yl)-ethyl ketone (4-bromobiphenyl-4'-yl)-n-propyl ketone, 4-bromobiphenyl-4'-carbamic acid ethyl ester, 4 bromostilbene-4'-carboxylic acid methyl ester, 4-bromostilbene-4'-carboxylic acid ethyl ester, 4-bromostilbene-4'-carboxylic acid n-propyl ester, 4-bromostilbene-4'-carboxylic acid n-butyl ester, 4-bromostilbene-4'-carboxylic acid i-propyl ester, 4-bromostilbene-4'-carboxylic acid i-butyl ester, 4-bromostilbene-4'-carboxylic acid tert.-butyl ester, 4-bromo-4'-nitrostilbene, 4-acetoxy-4'-bromostilbene, 4-bromostilbene-4'-tetrahydropyranyl ether, 4-bromo-4'-iodostilbene, 4,4'-dibromostilbene, 4-bromo-4'-chlorostilbene, (4-bromostilbenyl-4')-methyl ketone, (4-bromostilbenyl-4')-ethyl ketone, (4-bromostilbenyl-4')-n-propyl ketone and 4-bromostilbene-4'-carbamic acid ethyl ester. The following are particularly preferred: 4-Bromobenzoic acid, 4-bromobenzoic acid methyl ester, 4-bromobenzoic acid ethyl ester, 4-bromobenzoic acid n-butyl ester, 4-bromobenzoic acid tert.-butyl ester, 4-bromonitrobenzene, 4-acetoxybromophenol, 4-bromophenyl-tetrahydropyranyl ether, 4-iodophenyl-tetrahydropyranyl ether, 1,4-dibromobenzene, 1-bromo-4-iodobenzene, 4-bromoacetophenone, (4-bromophenyl)ethyl ketone, 4-bromoacetanilide, 4-bromophenylcarbamic acid ethyl ester, 1-bromo-4-chlorobenzene, 4-bromobiphenyl-4'-carboxylic acid methyl ester, 4-bromobiphenyl-4'-carboxylic acid ethyl ester, 4-bromobiphenyl-4-carboxylic acid n-butyl ester, 4-bromobiphenyl-4'-carboxylic acid tert.-butyl ester, 4-bromo-4'-nitrobiphenyl, 4-acetoxy-4'-bromobiphenyl, 4-bromo-4'-iodobiphenyl, 4,4'-dibromobiphenyl, 4-bromo-4'-chlorobiphenyl, (4-bromobiphenyl-4'-yl)-methyl ketone, (4-bromobiphenyl-4'-yl)-ethyl ketone, (4-bromobiphenyl-4'-yl)-n-propyl ketone, 4-bromobiphenyl-4'-carbamic acid ethyl ester, 4-bromostilbene-4'-carboxylic acid ethyl ester, 4-bromostilbene-4-carboxylic acid n-propyl ester, 4-bromostilbene-4'-carboxylic acid tert.-butyl ester, 4-bromo-4'-nitrostilbene, 4-acetoxy-4'-bromostilbene, 4-bromostilbene-4'-tetrahydropyranyl ether, 4-bromo-4'-iodostilbene 4,4'-dibromostilbene 4-bromo-4'-chlorostilbene, (4-bromostilbenyl-4'-methyl ketone, (4-bromostilbenyl-4')-ethyl ketone, (4-bromostilbenyl,4')-n-propyl ketone and 4-bromostilbene-4'-carbamic acid ethyl ester.

Preferred compounds of formula (III) are those in which $R^5$ and $R^6$ stand for methyl or ethyl, e.g. 2-methyl-3-butyne-2-ol and trimethylsilylacetylene.

In the process according to the invention, about 0.8 to 1.2 mol preferably 1.0 to 1.2 mol of compound (III) is used per mol of compound of formula (II). Suitable palladium catalysts are described e.g. in R. F. Heck, Palladium Reagents in Organic Syntheses, Academic Press, New York 1985. Chapter 6, Section 6.8.1). The following are examples of suitable palladium catalysts: $Pd(OAc)_2$, $PdCl_2(P\phi_3)_2$, $Pd(OAc)_2(P\phi_3)_2$, $Pd(P\phi_3)_4$ and/or $PdCl_2$, used in a quantity of about 0.005 to 10 mol-%, preferably 0.05 to 5 mol-%, based on the aryl halide of formula (II) ($\phi$ denotes phenyl).

The compound which is basic in reaction may be used in excess in order to bind the hydrogen halide released in the reaction. The compound which is basic in reaction may also be used as diluent. Suitable compounds which are basic in reaction include, for example, secondary and/or tertiary amines such as diethylamine, diisopropylamine, piperidine, triethylamine, pyridine and N,N'-diethylaniline, salts of carboxylic acids such as potassium acetate, alkali metal carbonates such as potassium carbonate, alkali metal bicarbonates such as sodium bicarbonate, alkali metal alcoholates such as sodium methanolate and sodium ethanolate and alkali metal hydrides such as sodium hydride.

Copper(I) iodide, for example, may be used as cocatalyst for the reaction of compound (II) with compound (III). This cocatalyst may be added in a quantity of about 10 to 1000 mol-%, based on the quantity of palladium used. The activity of the catalyst may be further improved by the addition of phosphanes. Preferred phosphanes are, for example, triphenylphosphane and tri-o-tolylphosphane. The quantity of phosphanes to be used may easily be determined by preliminary tests. They are generally used in a quantity of about 100 to 1000 mol-%, based on the palladium put into the process.

It is in some cases advantageous to carry out the reaction according to the invention of compounds of formula (II) with compounds of formula (III) in the presence of a solvent and/or diluent. The following are examples of suitable solvents and diluents: Aromatic hydrocarbons such as benzene, toluene or xylene, ethers such as tetrahydrofuran or dioxane, alcohols such as methanol or ethanol, acetonitrile, dimethylsulphoxide, dimethylformamide and N-methylpyrrolidone as well as amines such as diethylamine or triethylamine. The solvents and/or diluents may be used singly or as mixtures. The quantity may vary within a wide range and a suitable quantity may easily be determined by preliminary tests.

It is sometimes also advantageous to carry out the reaction in an inert gas atmosphere, e.g. a nitrogen atmosphere. This depends, for example, on the starting materials used.

The compounds of formula (IX) obtained by the reaction of compounds of formula (II) with compounds of formula (III) are converted into acetylenes of the general formula (IV) by a treatment with compounds which are basic in reaction, optionally in suitable solvents and/or diluents. In this reaction, the group $R^4$ of the compounds of formula (IX) is replaced by hydrogen. Methods for such reactions have been described, e.g. by V.Jäger in Houben-Weyl, Vol. V/2a, pages 405 and 649.

The compounds which are basic in reaction may be, for example, alkali metal hydroxides such as sodium hydroxide and/or potassium hydroxide, alkali metal carbonates such as sodium carbonate and/or potassium carbonate and alkali metal hydrides such as sodium hydride. The quantity of basically reacting compounds to be used may easily be determined by preliminary tests and is normally from 1 to 100 mol-% preferably from 3 to 50 mol-%, based on the quantity of compound (IX) put into the process.

The following are examples of suitable solvents and/or diluents for the reaction described above: Aromatic hydrocarbons such as benzene, toluene or xylene, alcohols such as methanol or ethanol and mixtures of the above-mentioned solvents and/or diluents.

The reaction temperatures for the above-mentioned reaction depend to a large extent on the individual case. If the reaction is carried out in a solvent and/or diluent, the temperatures employed would generally be from $-20°$ C. to the boiling point of the solvent and/or diluent or mixtures used.

If $R^4$ in formula (IX) stands for $C(CH_3)_2$—OH, the acetone formed in the above described reaction may be continuously distilled off. If $R^4$ in formula (IX) stands for $Si(CH_3)_3$, the protective group may also be replaced by hydrogen by means of a treatment with potassium fluoride dihydrate or potassium fluoride in a suitable solvent and/or diluent such as methanol, ethanol and/or dimethylformamide.

In the process according to the invention, the compounds of formula (IV) are reacted with compounds of formula (V) at temperatures from 30° to 160° C., preferably at 40° to 130° C., optionally in an inert gas atmosphere, in the presence of a palladium catalyst and a compound which is basic in reaction, optionally in the presence of a cocatalyst, optionally a phosphane, and optionally in the presence of a solvent and/or diluent.

This reaction gives rise to diarylacetylenes corresponding to formula (X)

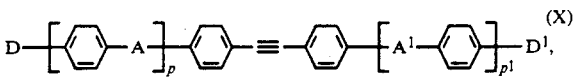

wherein D, $D^1$, A, $A^1$, p and $p^1$ have the meanings indicated above.

In the reaction of compounds of formula (IV) with the aromatic halides of formula (V) to form the diarylacetylenes of formula (X), from 0.7 to 1.3 mol, preferably from 0.8 to 1.2 mol of the compound of formula (IV) is generally used per mol of compound (V).

In the process according to the invention the compounds of formula (IV) may also be reacted with aromatic dihalides corresponding to the general formula (VIII)

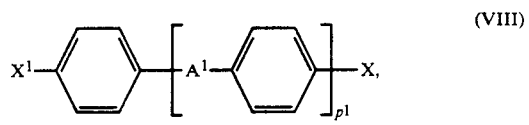

wherein $X^1$ and X and $A^1$ and $p^1$ have the meanings indicated above to form diacetylene compounds corresponding to formula (XI)

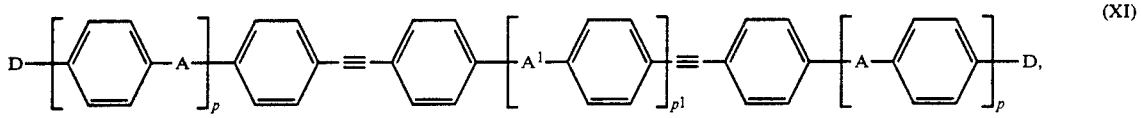

wherein D, A, $A^1$, p and $p^1$ have the meanings indicated above.

In that case, the compound of formula (IV) is generally used in a quantity of about 2.0 to 2.6 mol, preferably 2.0 to 2.2 mol, per mol of the compound of formula (VIII).

The reaction is again carried out at temperatures from 30° to 160° C. in the presence of a palladium catalyst and a compound which is basic in reaction, as described above.

The following are examples of preferred compounds of formula (VIII): 1,4-Diiodobenzene, 1-bromo-4-iodobenzene, 1,4-dibromobenzene, 4,4'-diiodobiphenyl, 4-bromo-4'-iodobiphenyl, 4,4'-dibromobiphenyl, 4,4'-diiodostilbene, 4-bromo-4'-iodostilbene and 4,4'-dibromostilbene, the following being particularly preferred: 1,4-dibromobenzene, 4,4'-dibromobiphenyl and 4,4'-dibromostilbene.

As regards the palladium catalyst, the base, the cocatalyst and the addition of phosphane and diluent or solvent, the same applies as already described for the reaction of compounds of formula (II) with compounds of formula (III).

The acetylenes of formula (X) obtained from the reaction and the diacetylenes of formula (XI) obtained are then reduced to the corresponding Z-stilbene compounds by means of hydrogen or other suitable reducing agents in the presence of catalysts. These Z-stilbene compounds are compounds corresponding to formula (VI):

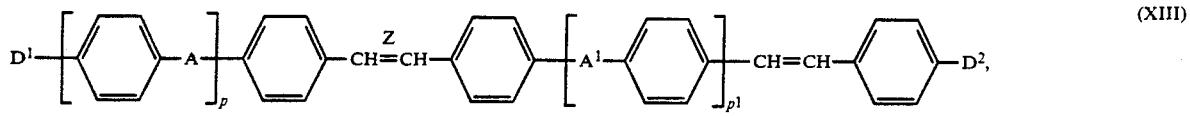

(XIII)

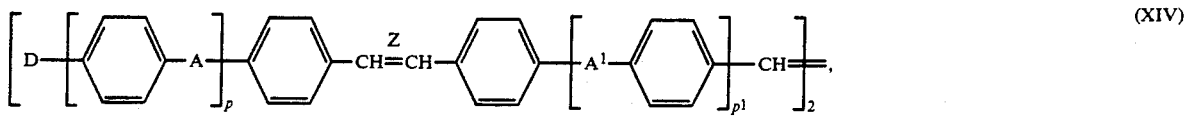

(XIV)

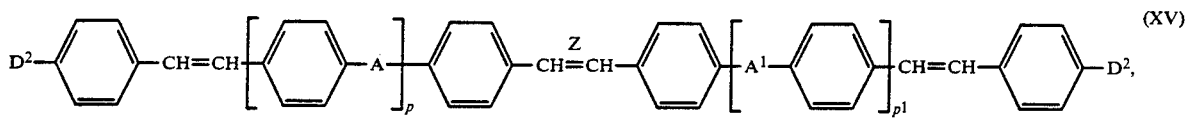

(XV)

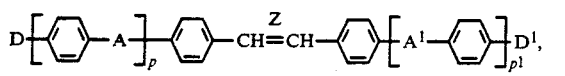

(VI)

wherein D, A, A¹, p and p¹ have the meanings already indicated and compounds corresponding to formula (XII)

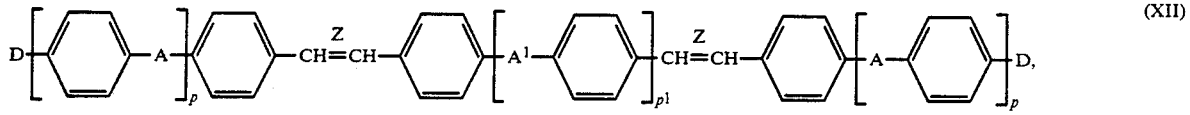

(XII)

wherein D, A, A¹, p and p¹ have the meanings already indicated.

The following are examples of suitable reduction processes: Hydrogenation in the presence of hydrogenation catalysts such as special palladium or nickel catalysts which have been described, for example, by H. Balli in Houben-Weyl, Vol. V/1b, pages 588 et seq; by H. Gutmann and H. Lindlar in Chemistry of Acetylenes, H. G. Viehe Ed., Marcel Dekker, New York 1969, pages 355 et seq; and by J. J. Brunet and P. Caubere in J.Org.Chem. 49, 4058 (1984); reduction with systems of metal and agents which split off protons, such as the reduction with zinc or zinc/copper pairs in acetic acid, alcohol or water (described e.g. by H. Balli in Houben-Weyl, Vol. V/1b, page 583; by B. L. Sondengam, G. Charles, and T. H. Akam, in Tetrahedron Lett. 1069 (1980); and by M. H. P. J. Aerssens, and L. Brandsma in J.Chem.Soc.Chem.Commun. 735 (1984); the conversion of acetylenes into vinyl silanes followed by stereoselective exchange of the silyl group for hydrogen (see e.g. D. G. Batt, and B. Ganem, in Tetrahedron Lett. 3323 (1978)) and the monohydroboration of acetylenes followed by protolysis, reduction with dialkyl aluminium hydrides or reduction with diimine (see H. Balli in Houben-Weyl, Vol. V/1b, pages 583 et seq).

When D and D¹ stand for at least one bromine atom, the compounds of formula (VI) may be reacted by the process according to the invention with compounds of formula (VII) in the presence of a palladium catalyst and a compound which is basic in reaction, optionally in the presence of a cocatalyst, optionally in the presence of a phosphane and optionally in the presence of a solvent and/or diluent at temperatures from 30° to 160° C., preferably at 40° to 130° C., optionally in an inert gas atmosphere, to produce compounds corresponding to the general formulae (XIII), (XIV) and (XV) in which D, A, p, A¹, p¹ and D¹ and D² have the meanings already indicated:

The reaction of aromatic halides, in particular aromatic bromides and iodides, with ethylene or ethylene derivatives is a known reaction (see e.g. R. F. Heck, Org. React. 27, 345 (1982)) and is carried out in the present invention by the conventional method.

The compounds corresponding to formula (VII) are well known compounds of organic chemistry or may easily be prepared by analogous processes (see e.g. W. Heitz et al, Makromol. Chem. 189, 119 (1988)).

The following are examples of preferred compounds corresponding to formula (VII): 4-Carboxystyrene, 4-carbomethoxystyrene, 4-carboethoxystyrene, 4-carbo-n-propoxystyrene, 4-carbo-i-propoxystyrene, 4-carbo-n-butoxystyrene, 4-carbo-i-butoxystyrene, 4-carbo-tert.-butoxystyrene, 4-acetaminostyrene, 4-acetoxystyrene, 4-nitrostyrene, (styry-4)methyl ketone, (styryl-4)ethyl ketone, (styryl-4)-n-propyl ketone, (styryl-4)-i-propyl ketone, (styryl-4)-n-butyl ketone, 4-chlorostyrene and 4-aminostyrene.

As a final step of the process according to the invention, the resulting Z-stilbene compounds containing the functional groups D, D¹ and D² are converted by basically known methods into the bifunctional stilbene compounds of formula (I) claimed according to the invention, which contain the functional groups Y and Z and have at least one Z-configurated stilbene group.

The conversion of the functional groups may be carried out, for example, by acid or alkaline hydrolysis of esters to the corresponding acids, by proton catalysed decomposition of tert.-butyl esters into free carboxylic acids and isobutene, by conversion of carboxylic acids into their chlorides, e.g. by a reaction with thionyl chloride or oxalyl chloride, optionally in the presence of catalytic quantities of DMF or pyridine, by the oxidation of aryl ketones to the corresponding aryl carboxylic acids, by the reduction of nitro groups to amino groups, by the conversion of amino or carboxyl groups into isocyanate groups or by the reaction of hydroxyl groups into the corresponding chlorocarbonic acid esters. These methods are well known and have been described e.g. in "Organikum", by a group of coauthors, VEB Deutscher Verlag der Wissenschaften, Berlin 1976; J. March, Advanced Organic Chemistry, Wiley, 3rd Ed. 1985; and C. Ferri, Reactionen der organischen Synthese, Stuttgart, Thieme 1978.

The process according to the invention may be represented by the following scheme of formulae which illustrates by way of example the synthesis of Z-1-(4-carboxyphenyl)-2-(4'-carboxybiphenyl-4-yl)ethene:

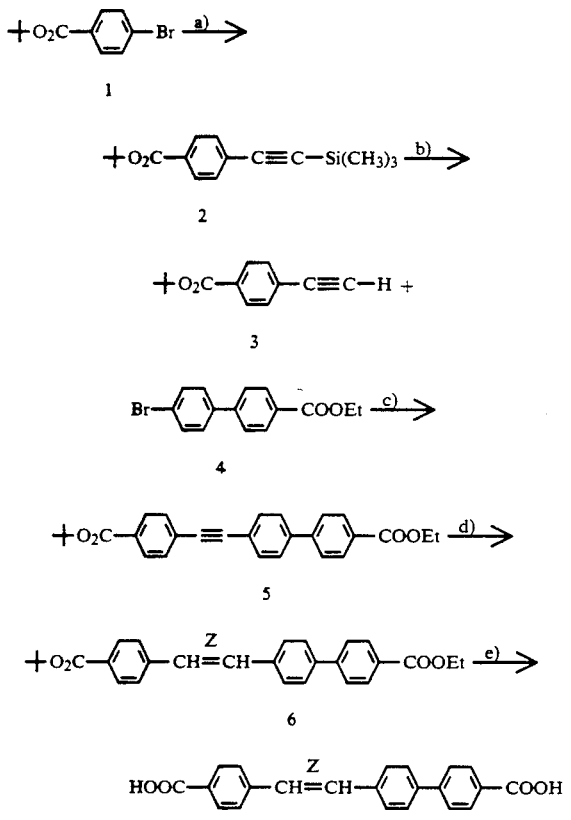

a) H—≡—Si(CH$_3$)$_3$, ($\phi_3$P)$_2$PdCl$_2$, CuI, $\phi_3$P, CH$_3$CN, NEt$_3$
b) K$_2$CO$_3$, CH$_3$OH
c) ($\phi_3$P)$_2$PdCl$_2$, CuI, $\phi_3$P, CH$_3$CN, NEt$_3$
d) Zn/Cu, C$_2$H$_5$OH, THF
e) 1. p-TsOH, Toluol, 2. NaOH, H$_2$O, C$_2$H$_5$OH 3. HCl Reactions e) 2. and 3. serve merely to purify the reaction product.

In one variation of the process according to the invention, aryl halides of formula (II) can be directly converted into the corresponding diarylacetylenes of formula (X) in which D=D$^1$, A=A$^1$ and p=p$^1$ and the symbols have the meanings already given for formula (X) by reacting the aryl halides of formula (II) with acetylenes of formula (III) in the presence of a palladium catalyst and a base, optionally in the presence of a cocatalyst, a phosphane, a solvent and/or diluent and a phase transfer catalyst at temperatures from 40° C. to 170° C., preferably at 60° C. to 130° C.

The aryl halides of formula (II) are preferably of the type given in the above list of aryl halides of formula (II).

The acetyl compound of formula (III) is preferably 2-methyl-3-butyn-2-ol.

In this variation, from 0.8 to 1.2 mol, preferably from 0.9 to 1.1 mol of acetylene of formula (III) are generally used for 2 mol of the aryl halide of formula (II). The palladium catalysts used are those already previously mentioned.

The reaction according to this variation is carried out in the presence of a compound which is basic in reaction. Examples of suitable compounds which are basic in reaction include alkali metal hydroxides such as sodium hydroxide and potassium hydroxide, alkali metal alcoholates such as sodium ethanolate and sodium methanolate, alkali metal hydrides such as sodium hydride, alkali metal amides such as sodamide, alkali metal carbonates such as sodium carbonate and potassium carbonate, alkali metal bicarbonates such as sodium bicarbonate and potassium bicarbonate, and mixtures of these compounds with one another. The reaction according to this variation may also be carried out in the presence of an aqueous solution of the above mentioned compounds which are basic in reaction. A co-catalyst may be used to accelerate the reaction. The co-catalysts already mentioned above are suitable for this purpose. Phosphanes may also be used for the reaction according to this variation. Suitable phosgenes have already been described above.

The reaction may be carried out in the presence of a solvent and/or diluent if necessary. Examples of suitable solvents and/or diluents include aromatic hydrocarbons such as benzene, toluene and/or xylene, amides such as dimethylformamide and/or NMP and/or sulphoxides such as dimethylsulphoxide and alcohols such as methanol and/or ethanol.

A phase transfer catalyst for the reaction of compounds of formula (II) with compounds of formula (III) may also be used in this variation. Suitable phase transfer catalysts are described, for example, by E. V. Dehmlow, and S. S. Dehmlow in Phase Transfer Catalysis. 2nd Edition, Verlag Chemie, Deerfield Beach. Fla., 1983. The following are suitable examples: Tetraethylammonium chloride monohydrate, tetraethylammonium bromide, tetraethylammonium iodide, tetraethylammonium tetrafluoroborate, tetraethylammonium-p-toluene sulphonate, allyl triethylammonium bromide, n-hexyl-trimethylammonium bromide, phenyl triethylammonium chloride, phenyltrimethylammonium iodide, benzyl trimethylammonium bromide, benzyl trimethylammonium iodide, n-octyl-trimethylammonium bromide, tetra-n-propylammonium bromide, tetra-n-propylammonium hydrogen sulphate, tetra-n-propylammonium trifluoromethanesulphonate, benzyl triethylammonium chloride, benzyl triethylammonium bromide, benzyl triethylammonium tetrafluoroborate, n-dodecyl trimethylammonium bromide, tetra-n-butylammonium chloride, tetra-n-butylammonium bromide, tetra-n-butylammonium iodide, tetra-n-butylammonium hydrogen sulpyhate, tetra-n-butylphosphonium bromide, tetraphenylphosphonium chloride, tetraphenylphosphonium bromide, tetraphenylphosphonium iodide, tetraphenylphosphonium hexafluoroantimonate, tetraphenylphosphonium tetrafluoroborate, N-hexadecylpyridinium bromide, tetra-n-hexylammonium bromide, tetra-n-hexylammonium hydrogen sulphate, n-hexadecyl-tri-n-butylphosphonium bromide, triphenylmethyl-triphenylphosphonium chloride, tetra-n-octylammonium bromide and tetra-n-dodecylammonium iodide.

It may be advantageous to carry out the reaction in an inert gas atmosphere, e.g. a nitrogen atmosphere.

In this variation, the reaction is generally carried out by introducing the aryl halide of formula (II), the acetylene of formula (III), the palladium catalyst, optionally the cocatalyst, the phosphane and the phase transfer catalyst into the reaction vessel, optionally in a suitable solvent and/or diluent, adding the compound which is basic in reaction and heating the reaction mixture to a sufficiently high temperature for the reaction. The components for the reaction may, of course, also be added in a different sequence. The acetylene of formula (III), optionally dissolved in one of the above-mentioned solvents and/or diluents, may be added dropwise to the other reactants at the reaction temperature within a suitable period of time, i.e. within about 0.5 to 24 hours. The progress of the reaction may be followed, for example, gas chromatographically. For working up the reaction product, the phases are generally separated and the reaction product is isolated by conventional methods. The reaction product in some cases already precipitates during the reaction or on cooling after termination of the reaction, in which case it is separated by suction filtration and the liquid phases are worked up by the usual methods. The reaction product may be purified by crystallisation, distillation or chromatography.

The reaction sequence of the process carried out according to this variation may be represented by the following scheme of formulae which illustrates by way of example the synthesis of Z-4,4′-stilbene dicarboxylic acid dichloride:

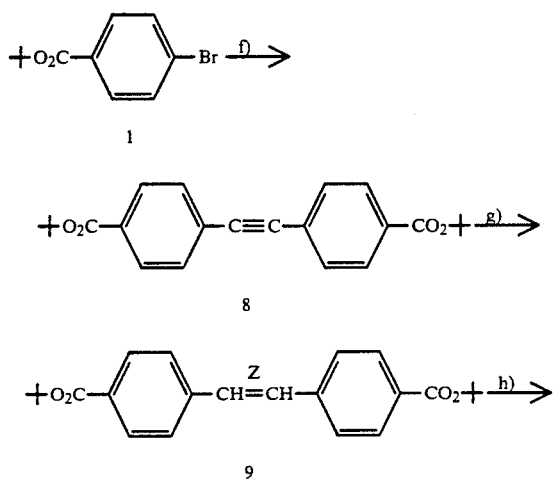

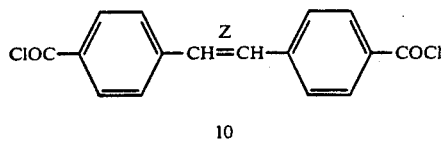

f) ≡─$+$OH, ($\phi_3$P)$_2$PdCl$_2$, CuI, P$\phi_3$, NaOH, H$_2$O, Toluene, BzNEt$_3$Cl
g) Zn/Cu, EtOH/THF
h) 1. p-TsOH, Toluene 2. NaOH, H$_2$O, EtOH 3. HCl 4. SOCl$_2$, DMF Steps h) 2. and 3. shown here serve merely for further purification of the reaction product.

According to another variation, compounds of formula (X) in which D≠D$^1$ and/or A≠A$^1$ and/or p≠p$^1$ may be prepared by the reaction of compounds of the general formula (IX) with aryl halides of the general formula (V) in the presence of a palladium catalyst and/or a compound which is basic in reaction, optionally in the presence of a cocatalyst, a phosphane, a solvent and/or diluent and a phase transfer catalyst at temperatures from 40° to 170° C., preferably at 60° to 130° C.

Preferred compounds of the formula (IX) are those in which R$^4$ is C(CH$_3$)$_2$—OH or Si(CH$_3$)CH$_3$.

Preferred compounds of formula (V) are those already mentioned in connection with formula (II).

As regards the palladium catalyst, the cocatalyst, the base, the diluent and/or solvent and the addition of phosphane and phase transfer catalyst, the same applies as has already been described for the above mentioned variation.

The quantity of aryl halide corresponding to formula (V) used is generally from 0.8 to 1.2 mol, preferably from 0.9 to 1.1 mol, per mol of the acetylene corresponding to formula (IX). The reaction of the compounds of formula (IX) with those of formula (V) may take place in the same manner as in the variation previously described.

This variation is therefore illustrated below by way of example for the synthesis of Z,E-1,4-bis-(4-carboxystyryl)-benzene:

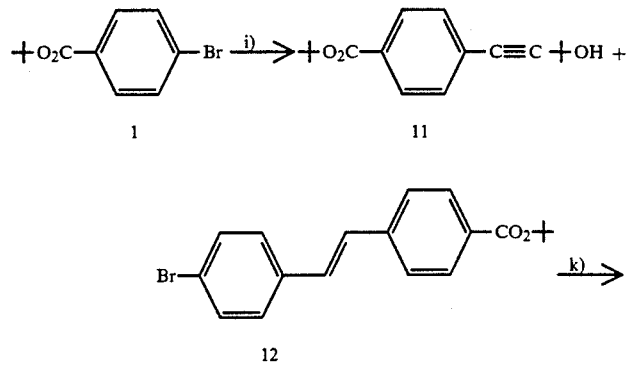

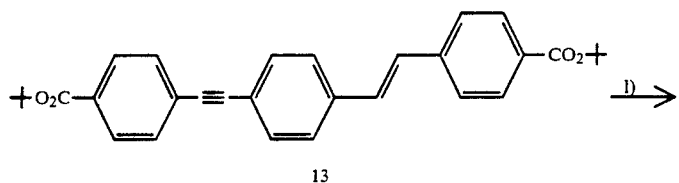
13
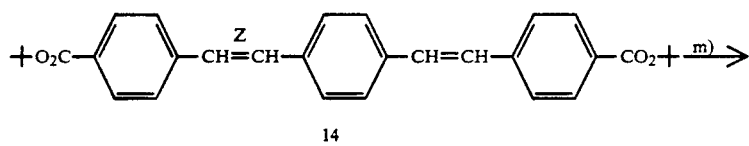
14
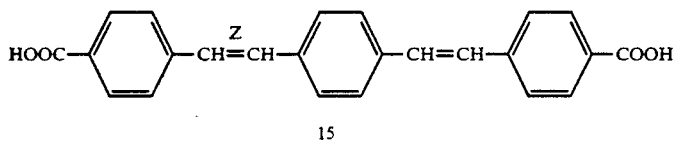
15
i) ≡—⬩OH, (Pϕ₃)₂PdCl₂, CuI, NEt₃, Pϕ₃, CH₃CN
k) (ϕ₃P)₂PdCl₂, CuI, Pϕ₃, NaOH, H₂O, Toluene, BzNEt₃Cl
l) Zn/Cu EtOH/THF
m) 1. p-TsOH, Toluene 2. NaOH, H₂O, EtOH 3. HCl
The reactions m) 2. and 3. serve to purify the reaction product.
This invention further relates to new Z-stilbene compounds corresponding to the following formulae:
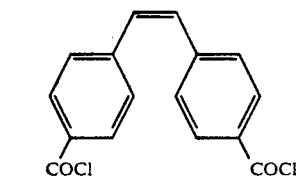
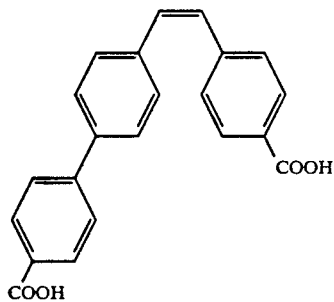
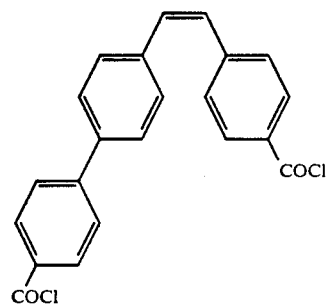
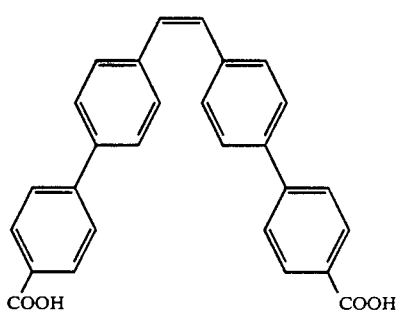
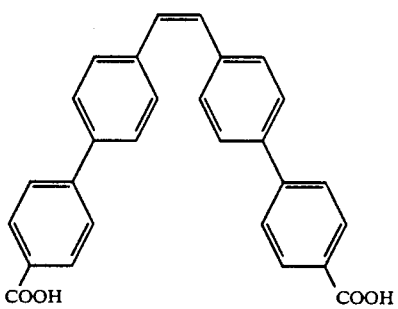
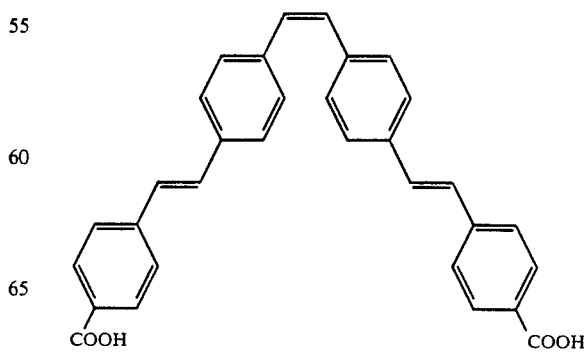

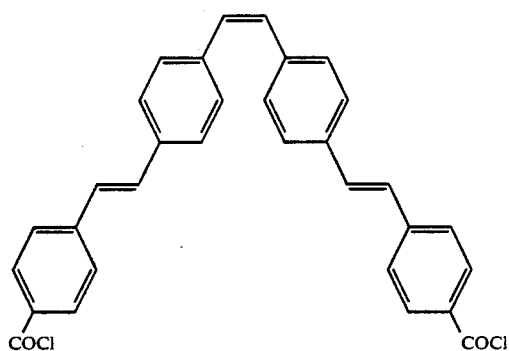

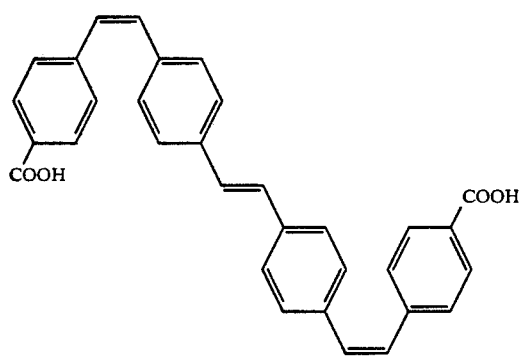

preferably

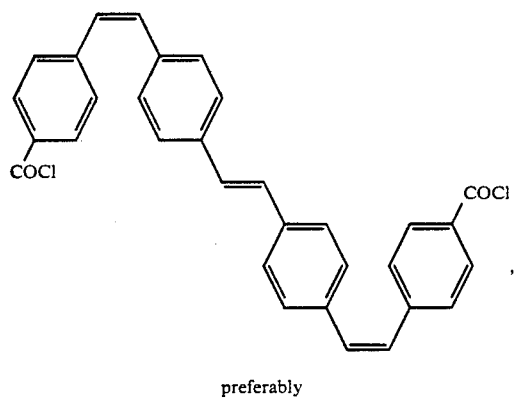

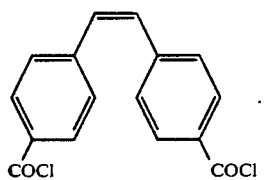

These new Z-stilbene compounds may be prepared by the process according to the invention described above or by its variations.

The bifunctional Z-stilbene compounds prepared by the process according to the invention are eminently suitable for the preparation of polymers such as polyesters, polyester carbonates, polyamides, polycarbonates, polyurethanes, polyethers and polyphenylene sulphides. Their special properties distinguish them advantageously from known isomeric stilbene derivatives which have hitherto been used for the synthesis of polymers containing stilbene fragments (see e.g. U.S. Pat. No. 4,654,412). Thus the solubility differences between bifunctional Z- and E-stilbene monomers in solvents used for the preparation of polymers by phase interface condensation is considerable.

It is possible, for example, to prepare an 11% solution of Z-stilbene-4,4'-dicarboxylic acid dichloride in dichloromethane whereas the chloride of the known E-stilbene-4,4'-dicarboxylic acid has a solubility of less than 1% and therefore cannot be used economically for a phase interface condensation, in contrast to the readily soluble Z-stilbene compound. It is obviously for this reason that processes for the preparation of polystilbene dicarboxylic acids by the phase interface condensation process have not hitherto become known. The bifunctional Z-stilbene compounds prepared according to the invention, which are in part new, have therefore made an important contribution to the manufacturing technique of both known and new materials containing polystilbene fragments, which materials are distinguished, for example, by their high temperature resistance.

EXAMPLES

Example 1

4-(Trimethylsilylethinyl)-benzoic acid tert.-butyl ester 51.4 g of Bromobenzoic acid tert.-butyl ester, 21.6 g of trimethylsilylacetylene, 1.4 g of $(Ph_3P)_2PdCl_2$ in 400 ml of absolute acetonitrile and 100 ml of triethylamine are stirred under reflux for 8 hours in an atmosphere of nitrogen. After the reaction product has been worked up with $CH_2Cl_2/H_2O$ and distilled, 40.6 g of 4-(trimethylsilylethinyl)-benzoic acid tert.-butyl ester are obtained.

Bp.$_{0.04\ mm}$: 120°–130° C.
Mp.: 60°–62° C.
NMR (CDCl$_3$): $\delta = 0.28$ (s, 9H), 1.63 (s, 9H), 7.53 (m, 2H), 7.95 (m, 2H).

Example 2

4-Ethinyl-benzoic acid tert.-butyl ester 274.4 g of 4-(trimethylsilylethinyl)-benzoic acid tert.-butyl ester and 12.5 g of anhydrous potassium carbonate in 1.5 l of absolute methanol are stirred together for 3 hours under nitrogen. The reaction mixture is then concentrated by evaporation and worked up with $CH_2Cl_2/H_2O$ to yield 194 g of 4-ethinyl-benzoic acid tert.-butyl ester.

Mp.: 70°–71° C.
NMR (CDCl$_3$): $\delta = 1.58$ (s, 9H), 3.22 (s, 1H), 7.52 (m, 2H), 7.94 (m, 2H).

Example 3

4,4'-Tolan-dicarboxylic acid-di-tert.-butyl ester

4-Bromo-benzoic acid tert.-butyl ester, 5.1 g of triphenylphosphine and 375 ml of NEt$_3$ are introduced into 1 l of absolute acetonitrile under nitrogen and N$_2$ is passed through the solution for 20 minutes. 10.5 g of $(P\phi_3)_2PdCl_2$ and 1.5 g of copper(I)iodide are then added and 166.5 g of 4-ethinyl-benzoic acid tert.-butyl ester dissolved in 1 l of absolute acetonitrile are slowly added dropwise under reflux and the reaction mixture is stirred overnight. The resulting reaction mixture is then suction filtered after cooling, stirred up in water, again suction filtered, dissolved in $CH_2Cl_2$ and filtered after the addition of a small quantity of Tonsil, and the solvent is then evaporated off under vacuum. 225 g of 4,4'-Tolan-dicarboxylic acid-di-tert.-butyl ester are obtained.

Mp.: 163° C.
NMR (CDCl$_3$): δ=1.60 (s, 18H), 7.58 (m, 4H), 7.98 (m, 4H)

Example 4

4,4'-Tolan-dicarboxylic acid di-tert.-butyl ester

A mixture of 514 g of 4-bromobenzoic acid tert.-butyl ester, 88.25 g of 2-methyl-3-butyn-2-ol and 74.5 g of triphenylphosphine in 1250 ml of toluene is added to 7.1 g of benzyl triethylammonium chloride, 9.55 g of copper(I)iodide and 14 g of (Pφ$_3$)$_2$PdCl$_2$ and the reaction mixture is stirred at reflux for 48 hours after the addition of 750 ml of 5.5 N NaOH. The organic phase is separated off, dried and concentrated by evaporation. 430 g of moist crude product are stirred up in 550 ml of methanol and suction filtered. 248 g of 4,4'-tolan-dicarboxylic acid di-tert.-butyl ester are obtained and may be further purified by recrystallisation from acetonitrile.

M.p. and NMR data correspond to those of the product obtained according to Example 3.

Example 5

Z-4,4'-Stilbene dicarboxylic acid di-tert.-butyl ester

52.6 g of Zn and 70 ml of ethanol are heated together with 13 g of 1,2-dibromoethane until evolution of gas ceases. A solution of 13 g of CuBr and 15.8 g of anhydrous LiBr in 70 ml of THF is added at 40° to 50° C. and the reaction mixture is stirred for 10 minutes. A hot solution of 50 g of 4,4'-tolan-dicarboxylic acid di-tert.-butyl ester in 70 ml of ethanol and 130 ml of THF is added and the mixture is heated under reflux for 72 hours. After filtration, the filtrate is concentrated by evaporation, taken up with CH$_2$Cl$_2$, washed twice with dilute HCl and H$_2$O, dried and concentrated by evaporation. 46.3 g of Z-4,4'-stilbene dicarboxylic acid di-tert.-butyl ester are obtained.

M.p.: 126°-127° C.
NMR (CDCl$_3$): δ=1.58 (s, 18H), 6.69 (s, 2H), 7.24 (m, 4H), 7.84 (m, 4H).

Example 6

Z-(4,4'-Stilbene dicarboxylic acid

331 g of Z-4,4'-Stilbene-dicarboxylic acid di-tert.-butyl ester in 1700 ml of absolute toluene are boiled under reflux for 3 hours together with 10.3 g of p-toluene sulphonic acid. The reaction mixture is then concentrated by evaporation and boiled under reflux for 4 hours with 104.2 g of NaOH, 1300 ml of H$_2$O and 1300 ml of ethanol. The reaction mixture is filtered hot after the addition of active charcoal, diluted with about 3 l of H$_2$O and extracted twice, in each case with 1 l of CH$_2$Cl$_2$. Concentrated HCl is then added to the aqueous phase. 230 g of Z-4,4'-stilbene dicarboxylic acid are obtained after suction filtration and drying.

M.p.: >280° C.
NMR (DMSO-d$_6$): δ=6.83 (s, 2H), 7.35 (m, 4H), 7.86 (m, 4H).

Example 7

Z-4,4'-Stilbene dicarboxylic acid dichloride

100 g of Z-Stilbene-4,4'-dicarboxylic acid, 400 ml of thionyl chloride and 3 drops of DMF are stirred at 40° C. until evolution of gas ceases. The product is then filtered under nitrogen and evaporated to dryness. 95 g of Z-4,4'-stilbene dicarboxylic acid dichloride are obtained.

M.p.: 102° C.
NMR (CDCl$_3$): δ=6.81 (s, 2H), 7.34 (m, 4H), 8.00 (m, 4H).

An even purer product is obtained by subsequently recrystallising the reaction product from an inert solvent such as cyclohexane, benzene or toluene and then optionally treating the resulting crystallised product again with thionyl chloride, optionally in a suitable solvent such as CH$_2$Cl$_2$.

Example 8

4-(4-Carbo-tert.-butoxyphenyl)-2-methyl-3-butyn-2-ol

257.1 g of 4-Bromobenzoic acid tert.-butyl ester, 168 g of 2-methyl-3-butyn-2-ol and 15.6 g of (Ph$_3$P)$_2$PdCl$_2$ in 1.5 l of absolute acetonitrile and 480 ml of triethylamine are stirred together at reflux for 6 hours under nitrogen. The product is then concentrated by evaporation and worked up with toluene/H$_2$O to yield 185 g of an oil which slowly crystallises.

NMR (CDCl$_3$): δ=1.60 (s, 9H), 1.65 (s, 6H), 7.43 (m, 2H), 7.92 (m, 2H).

Example 9

E-4-(Carbo-tert.-butoxy)-4'-(4-carbo-tert.-butoxystyryl)tolan

A mixture of 13.02 g of 4-(4-carbo-tert.-butoxyphenyl)-2-methyl-3-butyn-2-ol, 17.97 g of 4-bromo-4'-carbo-tert.-butoxystilbene, 0.93 g of triphenylphosphine. 0.34 g of benzyltriethylammonium chloride, 175 mg of bis(triphenylphosphine)palladium(II) chloride and 175 mg of copper(I) iodide in 70 ml of toluene and 36 ml of 5,5N NaOH is vigorously stirred under reflux for 48 hours. After the addition of 250 ml of saturated ammonium chloride solution, the reaction product is extracted with methylene chloride, dried and concentrated by evaporation.

Yield: 22.1 g

For characterisation see Example 10.

Example 10

E-4-(Carbo-tert.-butoxy)-4'-(4-carbo-tert.-butoxystyryl)tolan

300 ml of NEt$_3$ and 20.46 g of Pφ$_3$ are added under nitrogen to 234 g of 4-bromo-4'-carbo-tert.-butoxystilbene in 1 l of absolute acetonitrile. Nitrogen is passed through the stirred suspension for 20 minutes and 9.12 g of (Pφ$_3$)$_2$PdCl$_2$ and 2.5 g of copper(I)iodide are then added. 144 g of 4-Ethinyl benzoic acid tert.-butyl ester dissolved in 1 l of absolute acetonitrile are then added dropwise under reflux over a period of 6 hours and the reaction mixture is boiled under reflux overnight. The hot product obtained after suction filtration is dissolved in CH$_2$Cl$_2$, washed several times with H$_2$O and dried and the solvent is removed.

Yield: 275 g
Mp.: 218° C. (decomposition)
NMR (CDCl$_3$): δ=1.61 (s, 18H), 7.18 (s, 2H), 7.56 (m, 8H), 7.98 (m, 4H).

Example 11

Z,E-1,4-Bis-(4-carbo-tert.-butoxystyryl)-benzene

272 g of zinc dust in 270 ml of tert.-butanol are boiled with 24.9 ml of 1,2-dibromoethane until evolution of gas ceases. 55.5 g of CuBr and 66.9 g of LiBr in 200 ml of THF are then carefully added at 50° C. When the exothermic reaction has died down, 272 g of E-4-(carbo-tert.-butoxy)-4'-(4-carbo-tert.-butoxy-styryl)-tolan in 1.7 l of THF and 560 ml of tert.-butanol are added and the reaction mixture is heated under reflux for 4 days. The resulting reaction mixture is then evaporated to dryness, taken up in $CH_2Cl_2$ and filtered and the filtrate is washed with dilute HCl, dried and concentrated by evaporation.

Yield: 247 g
Mp: 125° C.
NMR ($CDCl_3$): $\delta = 1.59$ (s, 9H), 1.61 (s, 9H), 6.65 (m, 2H), 7.13 (m, 2H), 7.23 (m, 2H), 7.31 (m, 2H), 7.40 (m, 2H), 7.51 (m, 2H), 7.86 (m, 2H), 7.96 (m, 2H).

Example 12

Z,E-1,4-Bis-(4-carboxy-styryl)-benzene 131 g of Z,E-1,4-Bis-(4-carbo-tert.-butoxy-styryl)benzene are boiled under reflux with 6.5 g of p-toluenesulphonic acid in 1 l of toluene for 3 hours. The reaction product is evaporated to dryness and heated for a further 4 hours with 30 g of NaOH in 300 ml of water and 600 ml of ethanol. The ethanol is distilled off and the residue is acidified (conc. HCl) after dilution with water. The product is suction filtered and dried.

Yield: 96 g
NMR (DMSO-$d_6$): $\delta = 6.74$ (m, 2H), 7.25 (m, 2H), 7.30-7.45 (m, 4H), 7.54 (m, 2H), 7.70 (m, 2H), 7.86 (m, 2H), 7.96 (m, 2H), 12.9 (broad, OH).

Example 13

1-(4-Carbo-tert.-butoxyphenyl)-2-(4'-carbethoxy-biphenyl-4-yl)-ethyne 100 ml of triethylamine, 6.3 g of triphenylphosphine, 2.81 g of $(P\phi_3)_2PdCl_2$ and 0.77 g of copper(I)iodide are added under nitrogen to 61 g of 4-bromo-4'-carbethoxybiphenyl in 300 ml of absolute acetonitrile. 44.3 g of 4-ethinyl-benzoic acid tert.-butyl ester dissolved in 300 ml of absolute acetonitrile are slowly added dropwise at the reflux temperature and the reaction mixture is boiled overnight. It is then suction filtered while hot and stirred up in water and again suction filtered and the residue is dissolved in $CH_2Cl_2$ and filtered after the addition of Tonsil.

Yield: 73.2 g
Mp.: 169°–170° C.
NMR ($CDCl_3$): $\delta = 1.41$ (t, 3H), 1.60 (s, 9H), 4.41 (q, 2H), 7.58 (m, 2H), 7.63 (s, 4H), 7.68 (m, 2H), 7.98 (m, 2H), 8.13 (m, 2H).

Example 14

Z-1-(4-Carbo-tert.-butoxyphenyl)-2-(4'-carbethoxybiphenyl-4-yl)ethene 50.6 g of zinc, 54 ml of absolute ethanol and 10.7 ml of 1,2-dibromoethane are boiled until evolution of gas ceases. A solution of 10.7 g of CuBr and 12.7 g of LiBr in 54 ml of absolute THF is then added at 50° C. After 5 minutes, 47.8 g of 1-(4-carbo-tert.-butoxyphenyl)-2-4'-carbethoxybiphenyl-4-yl)-ethyne in 100 ml of absolute THF and 30 ml of absolute ethanol are added and the reaction mixture is boiled under reflux for 5 days. The product is then suction filtered, concentrated by evaporation and worked up with $CH_2Cl_2$/1 N HCl.

Yield: 31.2 g
NMR ($CDCl_3$): $\delta = 1.40$ (t, 3H), 4.40 (q, 2H), 6.72 (m, 2H), 7.31 (m, 2H), 7.38 (m, 2H), 7.53 (m, 2H), 7.65 (m, 2H), 8.00 (m, 2H) 8.10 (m, 2H).

The signals partly overlap.

Example 15

Z-1-(4-Carboxyphenyl)-2-(4'-carboxybiphenyl-4-yl)-ethene 31.2 g of 1-(4-Carbo-tert.-butoxyphenyl)-2-(4'-carbethoxybiphenyl-4-yl)-ethene in 150 ml of absolute toluene are boiled under reflux for 3 hours with 1 g of p-toluene sulphonic acid. The reaction mixture is then evaporated to dryness, 8.68 g of NaOH in 100 ml of $H_2O$ and 100 ml of ethanol are added, and the mixture is boiled for 4 hours. It is then filtered hot after the addition of active charcoal, diluted with 200 ml of $H_2O$ and extracted twice with $CH_2Cl_2$, and the product is precipitated from the aqueous phase with conc. HCl.

Yield: 17.75 g
NMR (DMSO-$d_6$): $\delta = 6.78$ (m, 2H), 7.34 (m, 2H), 7.40 (m, 2H) 7.67 (m, 2H), 7.80 (m, 2H), 7.88 (m, 2H) 8.04 (m, 2H), 12.91 (broad) OH).

Example 16

4-Bromotolan-4'-carboxylic acid-tert.-butyl ester 2.8 g $(Ph_3P)_2PdCl_2$ and 400 mg of CuI are added to a solution of 40.4 g of 4-ethinyl-benzoic acid tert.-butyl ester, 56.6 g of bromoiodobenzene and 1.34 g of $Ph_3P$ in 50 ml of diethylamine and 300 ml of absolute acetonitrile and the reaction mixture is stirred for 72 hours at 40° C., suction filtered and dried.

Yield: 50.5 g
Mp.: 115°–116° C.
NMR ($CDCl_3$): $\delta = 1.59$ (s, 9H, 7.3-7.6 (m, 6H), 7.96 (m, 2H).

Example 17

Z-4-Bromo-4'-carbo-tert.-butoxystilbene 56 g of Zn and 14 g of 1,2-dibromoethane are boiled in 70 ml of ethanol until evolution of gas ceases. 14 g of copper bromide and 16.8 g of lithium bromide in 70 ml of THF are then added, followed by 50 g of 4-bromotolan-4'-carboxylic acid tert.-butyl ester in 250 ml of THF and 50 ml of ethanol and the reaction mixture is boiled under reflux for 44 hours. The resulting reacting mixture is filtered, concentrated by evaporation, taken up with $CH_2Cl_2$, washed with dilute hydrochloric acid, dried and concentrated by evaporation.

Yield: 40 g somewhat contaminated with Z-4-stilbenecarboxylic acid tert.-butyl ester.

Example 18

Z,E,Z-1,2-Bis-(4-carbo-tert.-butoxystilbenyl-4')-ethene

Ethylene is passed through a solution of 17.9 g of Z-4-bromo-4'-carbo-tert.-butoxystilbene, 9.82 g of potassium acetate, 0.91 g of triphenylphosphine and 0.11 g of $(P\phi_3)_2PdCl_2$ in 150 ml of absolute DMF at 100° C. The reaction mixture is diluted with water, extracted with ether, thoroughly washed several times with water, dried and concentrated by evaporation and the residue is stirred up with petroleum ether.

Yield: 3.2 g
NMR ($CDCl_3$): $\delta = 1.55$ (s, 18H), 7.62 (m, 4H), 7.02 (s, 2H), 7.15-7.45 (m, 12H), 7.86 (m, 4H).

We claim:

1. New Z-stilbene compounds corresponding to the following formulae

23
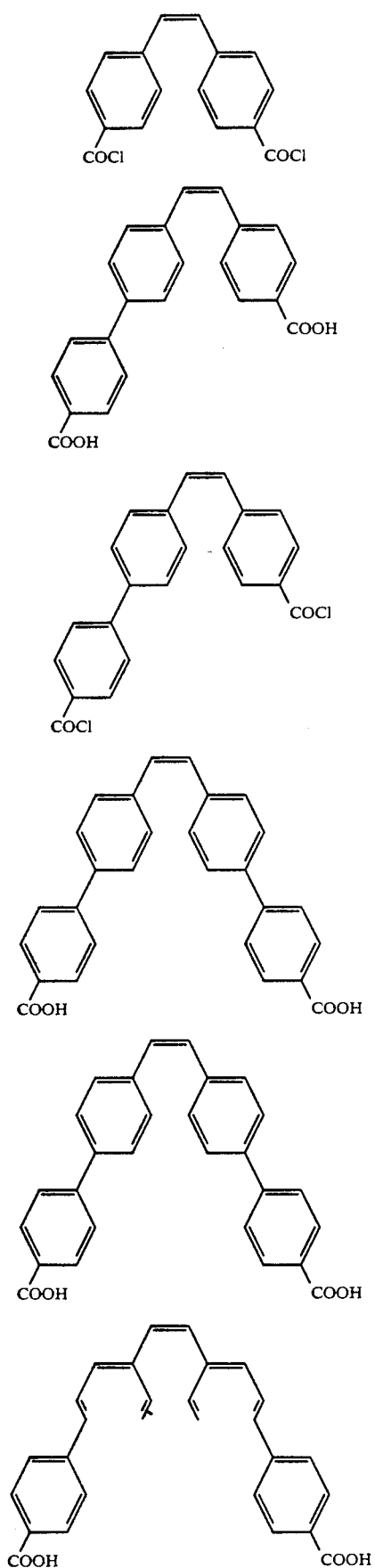
24
-continued
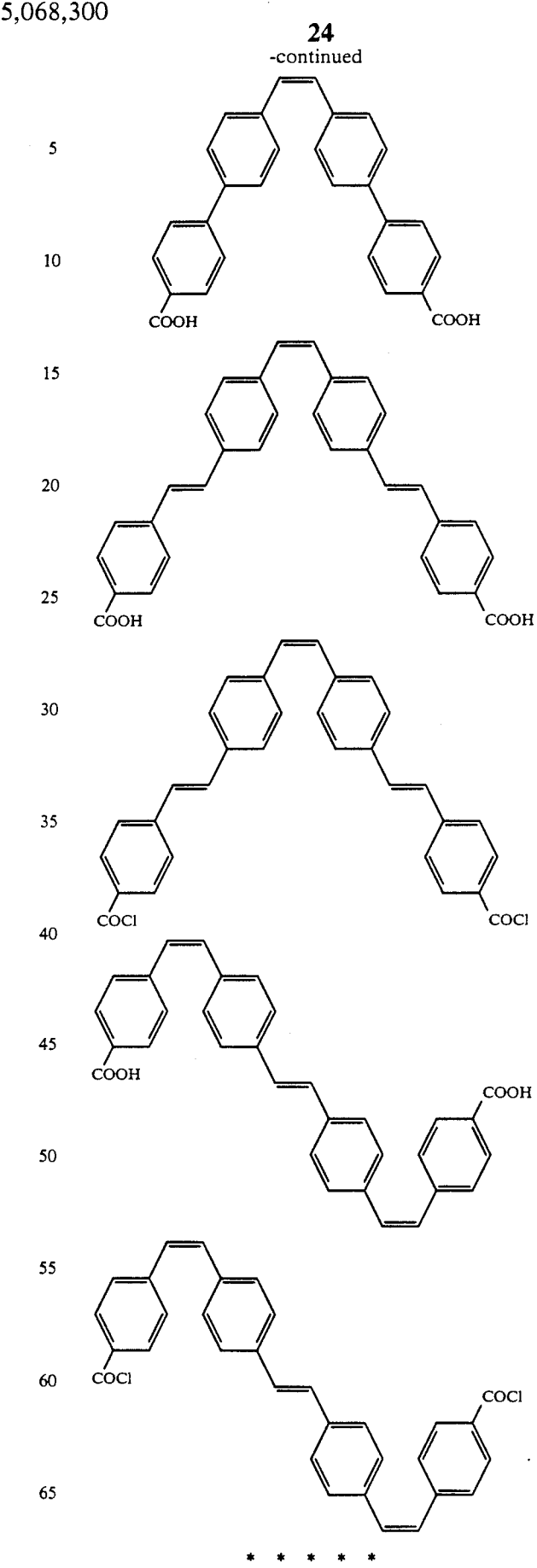
* * * * *